United States Patent
Cox et al.

(10) Patent No.: US 11,545,240 B2
(45) Date of Patent: Jan. 3, 2023

(54) COMPUTER IMPLEMENTED PROCESS CONTROL USING A COMPUTER INSTANTIATED MATHEMATICAL MODEL DEFINING SEQUENCED-BASED ANCHORING AND TIME- BASED ANCHORING BETWEEN NODES

(71) Applicant: SIGNALPATH, LLC, Raleigh, NC (US)

(72) Inventors: Alan Cox, Apex, NC (US); Jason Crocker, Raleigh, NC (US); Brent Johnson, Raleigh, NC (US); Kevin Monroe, Mebane, NC (US); Matthew Tibbit, Durham, NC (US)

(73) Assignee: SignalPath, LLC, Raleigh, NC (US)

( * ) Notice: Subject to any disclaimer, the term of this patent is extended or adjusted under 35 U.S.C. 154(b) by 332 days.

(21) Appl. No.: 16/034,320

(22) Filed: Jul. 12, 2018

(65) Prior Publication Data
US 2020/0020422 A1 Jan. 16, 2020

(51) Int. Cl.
*G16H 10/20* (2018.01)
*G06F 9/50* (2006.01)

(52) U.S. Cl.
CPC ........... *G16H 10/20* (2018.01); *G06F 9/50* (2013.01)

(58) Field of Classification Search
CPC .......... G16H 10/20; G16H 40/20; G06F 9/50; G06Q 50/20; G06Q 50/24
See application file for complete search history.

(56) References Cited

U.S. PATENT DOCUMENTS 7,054,823 B1 * 5/2006 Briegs .................... G16H 10/20
  705/2
8,400,467 B1 * 3/2013 Ponce de Leon ...........................
  G06Q 10/06316
  345/619

(Continued)

FOREIGN PATENT DOCUMENTS

CA 2853627 A1 5/2013
WO 2018077016 A1 5/2018
(Continued)

OTHER PUBLICATIONS

Spectrum Health, Specimen Collection, Jan. 2017, Centrifuge & Aliquot, Slides 4, 6, 8. (Year: 2017).*

(Continued)

*Primary Examiner* — Rachelle L Reichert
*Assistant Examiner* — Amanda R. Covington

(57) ABSTRACT

A computer method of managing a workflow of scheduled nodes. The method comprises instantiating a computer instantiated mathematical model of workflow paths, wherein the mathematical model defines nodes to be scheduled, defines time-based anchors between the nodes, and sequence-based anchors between the nodes; for each workflow object, determining a workflow schedule for the workflow object by an application executing on a computer system, wherein the workflow schedule comprises a plurality of nodes and wherein the application determines the workflow schedule based on the time-based anchors and sequence-based anchors between nodes defined by the mathematical model; storing by the application context information about completion of the activities performed when performing the node associated with the workflow path of the workflow object; and changing the workflow schedule of the workflow object based on the context information about completion of the activities performed and based on the mathematical model.

18 Claims, 10 Drawing Sheets

(56) References Cited

U.S. PATENT DOCUMENTS

| | | | |
|---|---|---|---|
| 8,688,475 B2 | 4/2014 | Ferguson | |
| 2005/0209993 A1* | 9/2005 | Koehler | G06Q 10/0633 |
| 2007/0250344 A1* | 10/2007 | Stephenson | G16H 10/20 |
| | | | 705/2 |
| 2009/0264955 A1* | 10/2009 | Giftakis | G16H 40/40 |
| | | | 607/45 |
| 2014/0316822 A1* | 10/2014 | Kleeman | G06F 40/143 |
| | | | 705/3 |
| 2014/0330572 A1* | 11/2014 | Bockelman | G16H 10/20 |
| | | | 705/2 |
| 2015/0154361 A1* | 6/2015 | Barsoum | G16H 80/00 |
| | | | 705/3 |
| 2018/0158541 A1* | 6/2018 | Baniameri | G16H 10/60 |
| 2020/0327481 A1* | 10/2020 | Allouche | E21B 41/00 |

FOREIGN PATENT DOCUMENTS

| | | |
|---|---|---|
| WO | WO2018/077016 A1 * | 5/2018 |
| WO | 2020013920 A1 | 1/2020 |

OTHER PUBLICATIONS

Cox, Alan, et al., "Computer Implemented Process Control Using Cycle Objects in a Computer Instantiated Mathematical Model Defining Sequence-Based Anchoring and Time-Based Anchoring Between Nodes," filed Nov. 1, 2019, U.S. Appl. No. 16/672,425.

Foreign Communication from a Related Counterpart Application, International Search Report and Written Opinion dated Sep. 24, 2019, International Application No. PCT/US19/33605 filed on May 22, 2019.

Foreign Communication From a Related Counterpart Application, International Report on Patentability dated Jan. 21, 2021, Application No. PCT/US19/33605 filed May 22, 2019.

* cited by examiner

COMPUTER IMPLEMENTED PROCESS CONTROL USING A COMPUTER INSTANTIATED MATHEMATICAL MODEL DEFINING SEQUENCED-BASED ANCHORING AND TIME- BASED ANCHORING BETWEEN NODES

CROSS-REFERENCE TO RELATED APPLICATIONS

None.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Clinical trials are conducted to test new drugs, new medical devices, and new medical therapies. Clinical trials may be conducted by research coordinators at a plurality of different sites. The clinical trials typically are performed based on large textual documents referred to as protocols. Some protocols may define two or more arms for subjects of the trials to follow. For example, a first group of trial subjects may receive a placebo during the trial (a first arm of the protocol), a second group of trial subjects may receive a first dosage level of a medication (a second arm of the protocol), and a third group of trial subjects may receive a second dosage level of the medication (a third arm of the protocol). Sometimes a protocol defines criteria for admitting subjects to participate in a trial, for example a specific diagnosed medical condition or a specific experience of a medical event.

SUMMARY

In a computer method of managing a workflow of scheduled nodes is disclosed. The method comprises instantiating a computer instantiated mathematical model ("mathematical model") of workflow paths by an application executing on a computer system. The mathematical model defines a plurality of nodes to be scheduled by the application, defines time-based anchors that establish rules for computing time relationships between two or more of the nodes by the application, defines sequence-based anchors that establish rules for computing sequence relationships between two or more of the nodes by the application, and defines activities to be performed when completing the nodes. For each of a plurality of workflow objects, the application determines a workflow schedule for the workflow object, wherein the workflow schedule comprises a plurality of nodes to be performed in completing the workflow, wherein the application determines the workflow schedule based on a baseline date of the workflow object, based on the time-based anchors between nodes defined by the mathematical model, and based on the sequence-based anchors between nodes defined by the mathematical model, and wherein at least one node has a time-based anchor to a first node and has a sequence-based anchor to a second node. The application presents a list of activities to be performed when performing a node associated with a workflow path of a workflow object based on the mathematical model. The application stores context information about completion of the activities performed when performing the node associated with the workflow path of the workflow object. The application changes the workflow schedule of a third node associated with the workflow path of the workflow object on the context information about completion of the activities performed and based on the mathematical model. The application changes the workflow schedule of a plurality of other nodes of the workflow object based on the changed schedule of the third node, based on at least one time-based anchor between the third node and the other nodes associated with the workflow path of the workflow object, and based on at least one sequence-based anchor between the third node and the other nodes associated with the workflow path of the workflow object.

In another embodiment, a computer method of managing visits of subjects in a clinical trial is disclosed. The method comprises instantiating a computer instantiated mathematical model ("mathematical model") of clinical trial visits by an application executing on a computer system. The mathematical model defines a plurality of visits to be scheduled by the application, defines time-based anchors that establish rules for computing time relationships between two or more of the visits by the application, defines sequence-based anchors that establish rules for computing sequence relationships between two or more of the visits by the application, defines activities to be performed during the visits, and defines computational branches conditioned on context information about completion of activities performed during visits. For each of a plurality of subjects, the application determines a visit schedule for the subject, wherein a visit is associated with a plurality of activities to be performed in completing the visit, wherein the application determines the visit schedule based on a baseline visit date of the subject, based on the time-based anchors between visits defined by the mathematical model, and based on the sequence-based anchors between visits defined by the mathematical model, and wherein at least one visit has a time-based anchor to a first visit and has a sequence-based anchor to a second visit. The application presents a list of activities to be performed during a visit of a subject based on the mathematical model. The application stores context information associated with the subject, wherein the context information is about completion of the activities performed during the visit of the subject. The application changes the visit schedule of the subject based on evaluation of at least some of the stored context information in the condition of a computational branch defined by the mathematical model, wherein changing the visit schedule comprises removing at least one previously scheduled visit and adding at least one previously unscheduled visit. The application changes the schedule of a plurality of other visits of the subject based on the changed visit schedule of the subject, based on at least one time-based anchor between the at least one previously unscheduled visit and at least one other visit of the subject, and based on at least one sequence-based anchor between the at least one previously unscheduled visit and at least one other visit of the subject.

In yet another embodiment, a computer method of managing visits of subjects in a clinical trial is disclosed. The method comprises instantiating a computer instantiated mathematical model ("mathematical model") of clinical trial visits by an application executing on a computer system. The mathematical model is associated with a first clinical trial protocol and defines a plurality of visits to be scheduled by the application, each visit associated with a synchronization identity, defines time-based anchors that establish rules for computing time relationships between two or more of the visits by the application, defines sequence-based anchors that establish rules for computing sequence relationships between two or more of the visits by the application, defines activities to be performed during the visits, and defines computational branches conditioned on context information about completion of activities performed during visits. For each of a plurality of subjects, the application determines a visit schedule for the subject, wherein a visit is associated with a plurality of activities to be performed in completing the visit, wherein the application determines the visit schedule based on a baseline visit date of the subject, based on the time-based anchors between visits defined by the mathematical model, and based on the sequence-based anchors between visits defined by the mathematical model, and wherein at least one visit has a time-based anchor to a first visit and has a sequence-based anchor to a second visit. The application instantiates a second mathematical model of clinical trial visits by the application. The second mathematical model is associated with a second clinical trial protocol and the second mathematical model defines a plurality of visits to be scheduled by the application, each visit associated with a synchronization identity and where visits defined by the second mathematical model that are identical to visits defined by the mathematical model have the same synchronization identities, defines time-based anchors that establish rules for computing time relationships between two or more of the visits by the application, defines sequence-based anchors that establish rules for computing sequence relationships between two or more of the visits by the application, defines activities to be performed during the visits, and defines computational branches conditioned on context information about completion of activities performed during visits. For at least some of the plurality of subjects, the application determines a new visit schedule for the subject based on the visit schedule determined for the subject based on the mathematical model, based on the time-based anchors between visits defined by the second mathematical model and based on the sequence-based anchors between visits defined by the second mathematical model. The application presents a list of activities to be performed during a visit of a subject based on the second mathematical model. The application stores context information associated with the subject, wherein the context information is about completion of the activities performed during the visit of the subject.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
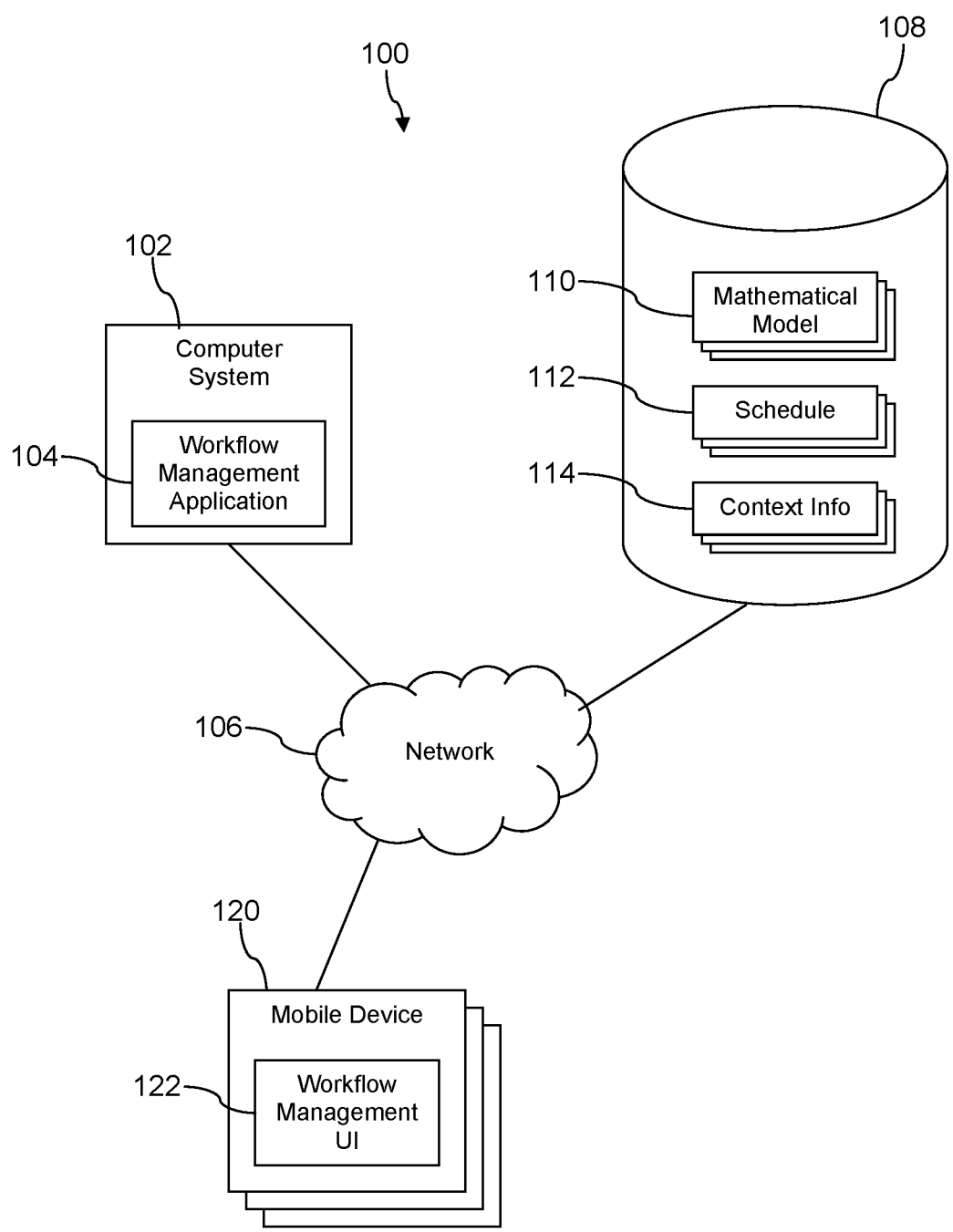
FIG. 1 is an illustration of a workflow management system according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

Clinical trials are defined by a protocol document that may be 50 pages in length, 200 pages in length, 300 pages in length, or longer. Clinical trials may be conducted to test a medication or to test a medical treatment process. The protocol document is a textual narrative that describes how to carry out a clinical trial. The protocol document may define different arms for subjects undergoing the clinical trial to follow. For example, one arm may be transited by subjects who receive a placebo and another arm may be transited by subjects who receive an active medication under trial. The protocol document defines visits that a subject of a clinical trial makes with research coordinators. The protocol document defines activities to perform during visits of the subjects. The protocol document defines events that may cause the subjects to follow a different path through the trial, for example based on a response of the subject to an activity performed during a visit. The protocol document defines constraints on visits of the subjects that may be specified both as a sequence constraint and as a timing constraint applied in relation to different visits. The protocol document may define time windows during which a visit desirably happens. As a subject progresses through the clinical trial, the subject's schedule of visits may stretch out or compress. As subjects pass through the clinical trial, different responses of subjects to activities performed during the visits may cause different subjects to branch onto different paths through the clinical trial. Different paths may feature visits that differ in various ways, for example differ in the activities performed and/or differ in the scheduling of the visits.

Because the protocol document may be long and complicated, research coordinators who work with subjects during their visits sometimes represent portions of the protocol documents with spreadsheets that may be adapted by attaching hand written sticky notes to the printed out spreadsheet pages or rely on other systems the entail extensive manual intervention to represent only a portion of the protocol. The research coordinators may use these printed out spreadsheets with attached sticky notes as a guide while conducting activities pursuant to a subject's visit. It becomes a complicated problem, using such an ad hoc system of spreadsheets and attached sticky notes, to keep subjects compliant with schedule constraints and to perform activities consistently in accordance with the protocol document, sometimes across multiple different research sites participating in the same clinical trial. A protocol document sometimes may be referred to as a protocol. In some cases sticky notes may provide only a rubric suggesting an activity that is to be performed without further cataloging the specific steps to be performed in the activity. Different research coordinators may interpret the curt rubrics differently and perform different steps when they should have been the same.

The present disclosure teaches a workflow management system that is tuned for clinical trials but that can be advantageously used outside of the clinical trial environment in other workflow management applications. The system comprises a workflow management application or workflow engine that is configured by a computer instantiated mathematical model constructed so as to represent a protocol document in a format useable by the workflow management application. The workflow management application executes on a computer system. The computer instantiated mathematical model can be considered to be a transcoding of the protocol document that is amenable to parsing by the workflow management application. The computer instantiated mathematical model defines a plurality of possible end-to-end paths through the clinical trial defined by the protocol. The computer instantiated mathematical model may define different protocol arms.

The computer instantiated mathematical model defines different branching points and subsequent paths that can be followed based on the occurrence or non-occurrence of protocol defined events and/or context information relating to the subject or activities completed during visits with the subject. For example, the computer instantiated mathematical model defines computational branches and associated branching conditions. The computational branches may be said to be conditioned on protocol events and/or on context information about completion of activities performed during visits. The computer instantiated mathematical model defines interrupts that may be incurred when protocol defined events happen, such as a subject experiencing a high level of liver toxicity and/or an adverse reaction to medication. The interrupt can shunt the subject onto a different path of visits. The interrupt can stall the subject in their progress on the current path of visits.

The computer instantiated mathematical model defines subject visits and relationships among the visits. The relationships among visits can be defined to be constrained by sequence and also constrained by time. More specifically, the computer instantiated mathematical model defines time-based anchors that establish rules for computing time relationships between two or more visits and defines sequence-based anchors that establish rules for computing sequence relationships between two or more visits. It is noted that the different types of anchors support anchoring a visit to two different visits, for example anchoring the visit with a time-based anchor to a first visit and anchoring the visit with a sequence-based anchor to a second visit that is different from the first visit.

The computer instantiated mathematical model may define cycles of visits, for example a set of visits that may repeat a predefined number of times or an indefinite number of times. The computer instantiated mathematical model defines activities that are to be performed during the visits. The cycle of visits may comprise two or more visits which repeat. For example, when in the cycle, a visit A may occur and then a visit B may occur; the visit A may occur again and then the visit B may occur again; the visit A may occur again and then the visit B may occur again. The cycle may be interrupted, for example, if a cycle exit condition is determined to be present, such as a subject is cured of a physical malady. The cycle may continue indefinitely until the subject dies or leaves the clinical trial to enter hospice care. In an embodiment, a cycle may comprise at least one visit which repeats (e.g., a cycle may comprise one or more visits which repeat). More broadly, a cycle of nodes may be defined that comprises two or more nodes which repeat. The cycle of nodes may be repeated until a cycle exit condition evaluates true. Alternatively, the cycle of nodes may be repeated indefinitely until the workflow is terminated for another reason, for example because the workflow object maintained by the computer system is destroyed or discarded. The nodes may be visits of a subject in a clinical trial. The nodes may be milestones to be completed in a project workflow. The nodes may be jobs to be completed by a workman or delivery man.

A research coordinator interacts with a subject, first to qualify and admit the subject to the clinical trial and second, optionally, to assign the subject to a protocol arm. After the subject is admitted to the clinical trial and optionally assigned to a protocol arm, the workflow management application, based in part on parsing the computer instantiated mathematical model, determines a schedule of visits of the subject that defines an end-to-end path of the subject through the clinical trial. The schedule of visits for the subject is determined based on a date of a baseline visit, based on time-based anchors among visits, and based on sequence-based anchors among visits. A baseline visit may be an initial visit when the subject is admitted to the clinical trial.

The portion of the end-to-end path of the subject through the clinical trial that has been completed may be referred to as completed visits or a completed visit path. These completed visits are represented by the workflow management application as data objects or data structures that may be stored in a non-volatile storage. The portion of the end-to-end path of the subject through the clinical trial that is uncompleted may be referred to as a projected visit path. The visits that comprise the projected visit path are also represented as data objects or data structures that are stored in the non-volatile storage. While the visit objects are being operated upon by the workflow management application, a copy of the visit objects may be retained in a volatile storage associated with a computer on which the workflow management application executes, such as random access memory (RAM). It is understood that as the subject progresses through the clinical trial, completing visits, the projected visit path of the subject may change, for example based on the subject's response to activities in the trial.

The research coordinator uses a mobile communication device, for example a tablet computer, to present a workflow management user interface (UI) that is communicatively coupled to the workflow management application. The workflow management UI provides controls and displays to assist the research coordinator in conducting subject visits. The workflow management UI allows the research coordinator to select a subject participating in the clinical trial. The workflow management UI allows the research coordinator to present a schedule of visits for a selected subject, for example a portion of the completed visit path of the subject comprising the last completed visit, the current visit, and a portion of the projected visit path of the subject comprising the next three projected visits. The workflow management UI may allow the research coordinator to move forwards in the list of visits and backwards in the list of visits, in a scrolling manner or in a sliding-window manner. The workflow management UI allows the research coordinator to click-on a visit and see a list of activities to be completed during the visit. The workflow management UI allows the research coordinator to click-on an activity and see a description of a procedure for completing the activity.

These various views and interactions provided to the research coordinator by the workflow management UI are mediated by or created by the workflow management application. The views and interactions are provided by the workflow management application based on parsing the computer instantiated mathematical model that is transcoded from the applicable protocol document and based on accessing the visit objects that have been created at a previous time by the workflow management application.

As the research coordinator conducts activities with the subject, data may be captured and stored by the workflow management application as context information or state information attached to the associated visit and/or to the subject. In an embodiment, the data is added to the associated visit data object or is attached to the visit data object, for example by a link and/or as metadata. For example, an activity may involve taking measurements of the vital signs of a subject. The values of these vital signs may be stored in a electronic data capture (EDC) system or in an electronic health record (EHR) system separate from the workflow management system. An indication that the activity was completed, a date the activity was completed, and a comment related to the subject may be stored as context attached to that visit by the workflow management application in response to the research coordinator capturing this context by using the workflow management UI. Context information may comprise indications that procedures of an activity have been completed, indications that activities have been completed, and/or indications that visits have been completed. Context information can include events and information about the events. Context information can include adverse events and serious adverse events. The workflow management application may analyze newly acquired context based on the computer instantiated mathematical model to advise on an altered projected visit path of the subject to complete the clinical trial.

The visit path determined by the workflow management application is determined based on anchors associated with visits defined in the computer instantiated mathematical model. The anchors can be of different types—a time-based anchor or a sequence-based anchor. An anchor is considered a dependence relationship of a visit. For example, a visit may have a dependence on another visit in the sense that the other visit must be completed before the visit. Alternatively, the visit may have a dependence on another visit in the sense that the visit must be completed no sooner than X days after completion of the other visit and no later than Y days after completion of the other visit. These dependencies are referred to as anchors herein. Thus, a visit may have a sequence-based anchor that anchors it to a first visit and may also have a time-based anchor that anchors it to a second, different visit. A visit may have one or more sequence-based anchors and/or one or more time-based anchors.

Time-based anchors may be of two types: forward time-based anchors and reverse time-based anchors. A forward time-based anchor is a time-based anchor where an anchor extends from a first visit (or node) to a second visit (or node), where the second visit is constrained to occur after the first visit by a designated time span. For example, the forward time-based anchor may constrain the second visit to occur at least 5 days after the first visit and not later than 9 days after the first visit. A reverse time-based anchor is a time-based anchor that extends from a third visit (or node) to a fourth visit (or node), where the third visit is constrained to occur before the fourth visit by a designated time span. For example, the reverse time-based anchor may constrain the third visit to occur no earlier than 9 days before the fourth visit and not later than 5 days before the fourth visit.

In some circumstances, a subject may miss a schedule window for a visit. For example, a subject may be scheduled to complete a visit 7 days plus or minus 2 days after the previous visit, but the subject comes in to the clinical site 10 days after the previous visit (e.g., a day later than the end of the time window). In an embodiment, the workflow management application prompts the research coordinator to decide if he wants to shift the schedule date for the present visit as well as other visits anchored to the present visit. If the shift is selected, the present visit is rescheduled—to the present time—and the other visits that are anchored to it, either in time or in sequence, have their schedules and anchoring dates pushed out accordingly.

Sometimes context information collected during a subject visit matches a condition of a computational branch defined by the mathematical model. Sometimes a subject experiences a protocol defined event that matches a branching condition defined by the mathematical model. When the workflow management application determines that a branching condition has occurred, it places the subject on a new visit path different from the projected visit path. Alternatively, the workflow management application determines that a branching condition has occurred, it notifies a research coordinator, and the research coordinator places the subject on a new visit path different from the projected visit path. The new visit path may not have some visits that had been defined for the projected visit path of the subject and may have other visits that were not defined for the projected visit path. The workflow management application, based on parsing the mathematical model, recalculates the projected visit path of the subject. For example, the workflow management application recalculates the projected visit path of the subject based on the time-based anchors and the sequence-based anchors of the visits that are defined for the new path the subject has been shifted into by the branching.

An interrupt may be considered to be related to a computational branch but is considered herein to be distinct. An interrupt in the processing by the workflow management application may be programmed into the rules implemented by the application to trigger or fire when special events occur. The interrupt may provide advice or guidance to a clinical researcher to alter a workflow of a subject in any of a variety of different ways. An interrupt may be invoked when a protocol defined event occurs, when an adverse event occurs, or when a serious adverse event occurs. From one point of view, an interrupt is invoked by an unanticipated event or an event exception. The interrupt interrupts the flow of a subject through the clinical trial. This interrupt may involve a delay the subject in progressing through the clinical trial, for example to undergo a washout period. This interrupt may involve adding one or more additional previously unscheduled visits and pushing out some previously scheduled visits. This interrupt may shunt the subject to a different branch of the workflow. This interrupt may shunt the subject to a different arm of the workflow. This interrupt may shunt the subject to an end of trial or out of the trial.

When a protocol changes from a first version to a second version, as is known to happen, the workflow management system is adapted for easy migration of subjects to the updated protocol by creating a new version of the computer instantiated mathematical model. Changes to a protocol may be changing trial candidate admission qualifications, changing instructions for activities, changing activities performed in a visit, changing a name of a visit, adding a visit, removing a visit, changing a dosage of a drug, and other changes. Visits of subjects defined in a computer instantiated mathematical model (in the original computer instantiated mathematical model and in the new version of the computer instantiated mathematical model) are assigned a synchronization identity (synch id). In the simplest scenario of a protocol version change, an end-to-end path for a subject that started a clinical trial under protocol A and is being transitioned to protocol B can be defined as the combination of a completed visit path associated with or completed in accordance with protocol A and a projected visit path associated with or defined in accordance with protocol B. The context remains attached to the completed visits after transition of the subject to protocol B.

Complexities in transferring a subject from protocol A to protocol B can arise in various ways, depending on the nature of the changes in protocol B. Some changes may relate to superficial changes to visits, such as changes of names of a visit. Those changes may be made by modifying the associated visit in the completed visit path by updating the synch id of the visit with the synch id of the visit as defined by the computer instantiated mathematical model associated with protocol B and completing the superficial change to the completed visit, such as changing the name in metadata associated to the visit. In some cases, protocol B may add visits that ought to have been completed. Those added visits may simply be added onto the start of the projected visit path and the schedule of the projected visits adapted accordingly. If visits completed under protocol A do not exist under protocol B, these visits and their associated context may be deleted from the completed visit path (although the history of these visits and their associated context may be stored in an archive).

The changes to the end-to-end visit path based on transitioning a subject from protocol A to protocol B is performed automatically by the workflow management application. In this way, subjects are easily transitioned from an earlier protocol to a later protocol, without the need to build new spreadsheets and recreate sticky notes to paste to printed out spreadsheets and without the need for manual intervention by sites and coordinators. The change is largely defined by creating the new computer instantiated mathematical model associated with protocol B, and this is simplified by starting the process of making the new computer instantiated mathematical model by copying the computer instantiated mathematical model of protocol A and then adapting it by retaining visits (which retain original synch ids), modifying visits (which receive new synch ids), and adding visits (which also receive new synch ids). Modifying a visit may include updating the anchors, the activities, and/or the instructions associated with the visit. When the newly created computer instantiated mathematical model is ready, the workflow management application automatically transitions or converts selected subjects from protocol A to protocol B.

When a subject has completed some activities, a research coordinator may attach a washout to the subject (e.g., attach a washout object or state to a computer representation of the subject using the workflow management UI). A washout state may be entered through an interrupt computational construct or artifact as described above. The washout state or object is responded to or processed by the workflow management application when it processes and/or presents visits associated with the subject. This washout state may be thought of as a processing interrupt or as an alternate processing branch performed by the workflow management application when supporting the workflow management UI interaction with a subject associated with the washout state or washout object. In this processing branch, the workflow management application may disallow some functions of the workflow management UI. Alternatively, in this processing branch, the workflow management application may add extra user input steps for completing research coordinator actions, for example prompting the research coordinator to acknowledge the washout state and to provide an explanation of why the research coordinator intends to push on with the visit or activity notwithstanding the washout state.

At a functional level, a washout may recommend deferring some following activities during a predefined time duration such as scheduling a visit that involves administering additional medication or that involves measuring physical properties of the subject or that involves completing a diagnostic procedure (e.g., an MRI, a CT scan, or other). A washout may prescribe some activities such as the subject drinking specified amounts of water daily, such as the subject eating foods from a predefined dietary regime. In some examples, a washout may be associated with waiting for a drug to be processed and evacuated by the body. A washout may be established at the initial entry of a subject to the clinical trial, as for example when the subject was taking some other drug prior to being admitted to the clinical trial. A washout may be established while the subject is in the middle of the clinical trial to remove or attenuate the presence of a drug in the subject's body. If a research coordinator pulls up an interface to the workflow management system on a device (e.g., a tablet or other mobile communication device) and attempts to schedule a visit during the washout period, the display will notify the research coordinator that the subject is in a washout. Likewise, if the research coordinator attempts to perform an activity that is contraindicated by a washout, the display will notify the research coordinator that the subject is in washout.

As an example, a subject may visit a clinic weekly on Tuesday mornings. During the previous visit, the subject may have had a strong drug administered and have been placed in washout for three weeks (e.g., should not have any further visits and/or activities performed during three weeks). Out of habit, the subject may return to the clinic the following Tuesday, notwithstanding the washout. This day, the research coordinator who usually meets with the subject may be away from the clinic on vacation, and a substitute research coordinator may be assigned to conduct the visit with the subject. When the substitute research coordinator pulls up the workflow management UI for the subject, a notification is presented that informs the substitute research coordinator that the subject is in washout and is restricted from receiving further medication and/or undergoing any further activities until the washout period is exited.

Turning now to FIG. 1, a workflow management system 100 is described. In an embodiment, the system 100 comprises a computer system 102 executing a workflow management application 104 or a workflow engine. The computer system 102 is communicatively coupled to a network 106, where the network 106 comprises one or more private networks, one or more public networks, or a combination thereof. The computer system 102 is communicatively coupled via the network 106 to a data store 108. The computer system 102 may comprise a plurality of computers or servers. Computer systems are described further hereinafter. The data store 108 may comprise or store a computer instantiated mathematical model 110, a plurality of subject visit schedules 112, and a plurality of context information objects 114. The computer instantiated mathematical model 110 may be associated with a clinical trial protocol. In some contexts, the computer instantiated mathematical model may be referred to as a mathematical model in the interests of concision. The schedules 112 may be associated with different subjects participating in a clinical trial associated with the mathematical model 110. Alternatively, the schedules 112 may be schedules for workers completing a work or project that extends over multiple periods or workdays. The schedules 112 may be schedules for teams of workers or a management project team collaborating to complete a project.

Each of the context information objects 114 may be associated with one of the subjects participating in the clinical trial associated with the mathematical model 110. Alternatively, the context information objects 114 may be associated with a workday or a milestone in an extended work or project to be completed. It will be appreciated that the system 100 is capable of managing a plurality of independent clinical trials concurrently, each clinical trial associated with its own mathematical model 110, its own plurality of subject visit schedules 112, and its own plurality of context information objects 114. In an embodiment, a single clinical trial may be associated with two or more mathematical models 110, for example when two or more protocol versions are associated with the same clinical trial.

The system 100 further comprises a plurality of mobile devices 120 where each mobile device 120 presents a workflow management user interface (UI) 122. A mobile device 120 may be a tablet computer, a notebook computer, a laptop computer, a mobile phone, a smart phone, a personal digital assistant (PDA), a wearable computer, a headset computer, or other portable communication device. The mobile device 120 is used by research coordinators to schedule subject visits, to conduct activities during subject visits, and to capture data and/or results from activities completed during subject visits. In an embodiment, results from activities completed during subject visits also may be captured in an electronic data capture (EDC) tool client (not shown) executing on the mobile device 120 and uploaded from the mobile device 120 via the network 106 to an EDC tool server (not shown), for example an EDC tool server managed by an organization sponsoring the clinical trial. In an embodiment, results from activities completed during subject visits also may be captured in an electronic health record (EHR) tool client (not shown) executing on the mobile device 120 and uploaded from the mobile device 120 via the network 106 to an EHR tool server (not shown), for example an EHR tool server managed by the organization sponsoring the clinical trial.

In an embodiment, the mobile devices 120 may be provided by the research site for use by the research coordinators. In an embodiment, the mobile devices 120 may be devices privately owned by research coordinators that have had the workflow management UI 122 installed on them. Alternatively, the mobile devices 120 may be devices privately owned by research coordinators that access the workflow management UI 122 as a web page presented by a browser application executing on the mobile device 120. The mobile devices 120 may be used by research coordinators working at the same research site (e.g., the same clinical site or doctor's office). Alternatively, some of the mobile devices 120 may be used by research coordinators working at different research sites. In an embodiment, the system 100 promotes consistency and accuracy of administration of the activities of a clinical trial by assuring that research coordinators working out of different research sites still adhere to the same mathematical model (e.g., adhere to the same clinical trial protocol, since the mathematical model is transcoded from the clinical trial protocol).

In an embodiment, the workflow management application 104 executes on computing resources of a cloud computing environment, the data store 108 is provided by cloud computing storage resources, and the workflow management functionality is delivered according to a software as a service (SaaS) model. The workflow management application 104 can be executed in a multi-tenant mode of operation, where different independent clinical trials are supported from the same multi-tenant workflow management application 104. The different clinical trials would be supported by different mathematical models.

The mathematical model 110 may be manually developed by trained technology workers based on a protocol document. The mathematical model 110 may be developed by trained technology workers based on a protocol document using a transcoding application that executes on the computer system 102, for example engaging in a computer-assisted transcoding process. Alternatively, the mathematical model 110 may be automatically generated by a transcoding application executing on a computer system, where the transcoding application converts the text of the protocol document into the mathematical model. For example, a protocol transcoding application executing on a computer system can parse the clinical trial protocol document, analyze the clinical trial protocol document based on the parsing, and automatically generate the mathematical model based on analyzing the parsed clinical trial protocol document.

Any number of mathematical models 110 may be stored in the data store 108. Multiple mathematical models 110 may be stored in the data store 108, wherein each different mathematical model 110 is transcoded from a different version of a protocol associated with the same clinical trial (e.g., a first mathematical model transcoded from a protocol A document associated with a first clinical trial, a second mathematical model transcoded from a protocol B document associated with the first clinical trial, and a third mathematical model transcoded from a protocol C document associated with the first clinical trial). Multiple mathematical models 110 may be stored in the data store, wherein each different mathematical model 110 is transcoded from different protocols associated with different clinical trials (e.g., a fourth mathematical model transcoded from a protocol D document associated with a second clinical trial, a fifth mathematical model transcoded from a protocol E document associated with a third clinical trial, a sixth mathematical model transcoded from a protocol F document associated with a fourth clinical trial).

The mathematical model 110 comprises a list of possible visits that may be completed by a subject of the clinical trial as well as definitions of computational branches and their associated branching conditions or branching criteria that may exist in end-to-end visit paths. The mathematical model 110 identifies dependencies or constraints among visits, for example sequence dependencies and time-based dependencies. These dependencies may be referred to as anchors, for example where a second visit is said to be anchored to a first visit. More specifically, the anchors may be referred to as time-based anchors and sequence-based anchors. These dependencies may be considered also to be one-way associations between visits, for example an association from a dependent visit to another visit.

In an embodiment, the time-based anchors and the sequence anchors may be built into a computer instantiated structure representing a visit, for example a visit class or a visit data structure. A visit class, for example, may have one or more time-based anchors and/or one or more sequence-based anchors. The anchor artifact (e.g., a part of the visit class or the visit object) identifies another visit class to which the anchor logically attaches or depends upon. The anchor artifact may further identify a numerical constraint, such as a minimum time interval and a maximum time interval after the visit to which the time-based anchor refers at which the visit is constrained to occur. In another embodiment, the visits and anchors may be implemented using different software engineering and/or computer programming paradigms or techniques.

The mathematical model 110 comprises lists of actions to be performed during each of the visits. The actions associated with a specific visit may be embedded in the definition in the mathematical model 110 of the visit class, for example as a method or as an action object having both data and methods. Such a method may present text that lists the actions and provides input controls for selection of one of the actions. The mathematical model 110 comprises descriptions of procedures for performing the actions. For example, the procedures may be embedded in a method invoked by selection of an action, and may present text describing the procedure and providing input controls for indicating the procedure step has been completed and/or indicating a value associated with the procedure step.

Some actions may, when completed, result in a washout being applied to a subject. A washout is an example of an interrupt, where interrupts were discussed above. Washouts may be defined by the mathematical model 110 in a variety of ways. The mathematical model 110 definition of a washout may define a washout criteria or condition, a washout duration, and/or washout instructions for a subject to perform while the washout state exists. For example, the washout condition may be administration of drug X. For example, a washout may define a time duration of 10 days, for example 10 days during which visits are not to take place while waiting for a previously administered drug time to be processed and evacuated by the subject. The washout instructions may include an instruction to drink at least 8 twelve ounce glasses of water per day, the washout instructions may identify a dietary regime to adhere to. The washout may be implemented as an object associated with a subject or a visit schedule 112 of a subject. Alternatively, the washout may be stored as a state in an object representing the subject or in the visit schedule 112. The washout causes the workflow management UI 122 to present a notification when information about the subject or the visit schedule 112 of the subject is called up on the display of the mobile device 120. In an embodiment, the workflow management UI 122 may prompt the research coordinator to acknowledge the washout, and this acknowledgement may be stored as context information objects 114.

The visits, computational branches, branching conditions, lists of actions, and descriptions of procedures are all extracted from or transcoded from the protocol document to make them amenable for parsing and executing by the workflow management application. In an embodiment, the mathematical model 110 is an electronic file that articulates all visits defined by a protocol as nodes and all possible anchors between visits as edges. Hence, in this embodiment, the protocol is transcoded as an abstract mathematical graph.

When processing or interacting with a visit schedule of a subject, the visits may be represented as nodes. A time-based anchor associated with nodes in a visit schedule of a subject may be represented as a time-based anchor edge, and a sequence-based anchor associated with nodes in a visit schedule of the subject may be represented as a sequence-based anchor edge. The workflow management application 104 and/or the mathematical model 110 may represent other relationships or associations in the mathematical model 110 and/or the visit schedule by edges.

In an embodiment, visits (e.g., nodes) are linked to activities, and activities are linked to procedures. In another embodiment, the protocol is transcoded as a structure or hierarchy of classes. In another embodiment, the protocol is transcoded as a database or a relational database comprising tables. In other embodiments, the mathematical model 110 is articulated in a different computer artifact format.

The workflow management application 104 processes the mathematical model 110 and information about a subject to generate an end-to-end visit path or visit schedule 112 for the subject. The workflow management application 104 constructs the end-to-end visit schedule 112 such that the schedules of visits satisfy both the sequence constraints and the timing constraints defined by the mathematical model 110. Said in another way, the workflow management application 104 constructs the end-to-end visit schedule 112 to maintain the sequence-based anchors and the time-based anchors defined for visits by the mathematical model 110. This visit schedule 112 is stored in the data store 108 and is revised by the workflow management application 104 as circumstances change. For example, the visit schedule 112 associated with a subject may be changed by the workflow management application 104 in response to new context information objects 114 associated with the subject, for example results of diagnostic activities or results from measurement of vitals of the subject. For example, the visit schedule 112 may be changed by the workflow management application 104 in response to transitioning the subject from a first version of a protocol to a second version of the protocol.

In another embodiment, the workflow management application 104 does not construct an end-to-end visit schedule 112 but only a portion of an end-to-end visit path, for example a portion of the end-to-end visit path that comprises the next several visits identified for the subject. In this embodiment, the workflow management application 104 doesn't construct the end-to-end visit schedule 112, because often this end-to-end visit schedule 112 will be modified because of events such as results the subject experiences in response to visit activities.

Figure 2:
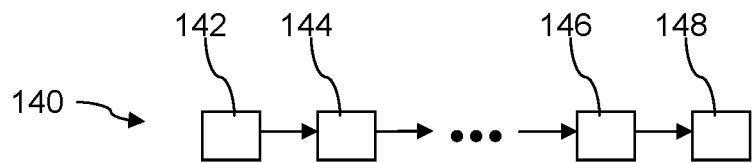
FIG. 2 is an illustration of a workflow according to an embodiment of the disclosure.

Turning now to FIG. 2, a visit schedule 140 is described. The visit schedule 140 comprises a first visit 142, a second visit 144, a third visit 146, and a fourth visit 148. The first visit 142 may be considered a baseline visit. During the first visit 142 the subject may undergo screening and be admitted to the clinical trial. Some candidates who undergo screening may be denied admittance to the clinical trial. A protocol document may specify qualifications for admitting a candidate to the clinical trial, such as having an age within a predefined age range, such as having experienced a protocol defined medical condition within a certain period of time prior to the first visit 142, and other criteria. Each visit may have a target date defined for when the visit with the subject is scheduled to occur as well as a time window around the target date during which completing the visit with the subject is acceptable. For example, the second visit 144 may have a target schedule date that is defined to be 7 days after the first visit 142, plus or minus 2 days. Thus, the subject could complete the second visit 5 days after and up to 9 days after the first visit 142.

Figure 3:
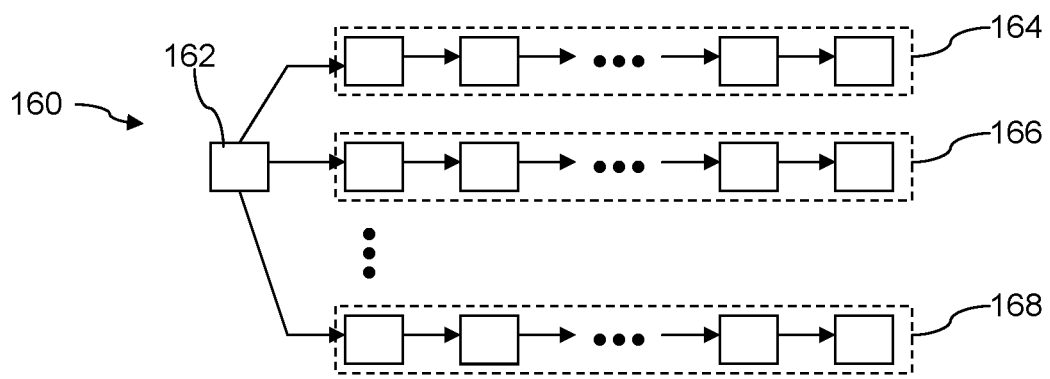
FIG. 3 is an illustration of a multi-arm workflow according to an embodiment of the disclosure.

Turning now to FIG. 3, a plurality of possible visit schedules 160 is described. A protocol may define a plurality of protocol arms such as a first protocol arm 164, a second protocol arm 166, and a third protocol arm 168. A subject who completes a screening visit 162 and is accepted into the clinical trial may be assigned to any of the three protocol arms 164, 166, 168. In an embodiment, the subject is randomly assigned to a protocol arm 164, 166, 168 by an activity referred to as randomization. In different protocol arms 164, 166, 168 different activities and possibly different visits are completed with subjects assigned to each protocol arm. For example, subjects on the first protocol arm 164 may receive placebos rather than active medication, subjects on the second protocol arm 166 may receive active medication at a half-dosage level, and subjects on the third protocol arm 168 may receive active medication at a full-dosage level.

Figure 4:
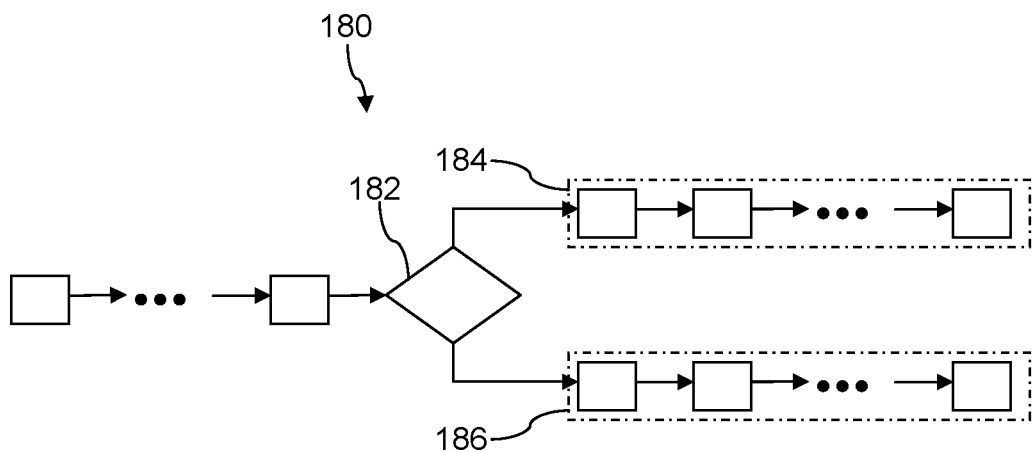
FIG. 4 is an illustration of a branch in a workflow according to an embodiment of the disclosure.

Turning now to FIG. 4, a visit schedule 180 that may take one of two different paths at a branching point is described. The visit schedule 180 has a branching point 182. Based on a decision, the visit schedule 180 proceeds on a first branch 184 or on a second branch 186. When the workflow management application 104 parses the branching point or computational branch defined by the mathematical model 110, it evaluates a condition defined for the computational branch by the mathematical model 110. The condition may identify an event. The condition may identify a threshold value of a metric or vitals indication associated with a subject, for example blood pressure above a first threshold value, O2 level less than a second threshold value, INR below a third threshold value. If the condition is not satisfied, the visit schedule of the subject may follow the first branch 184 defined by the mathematical model 110, and if the condition is satisfied, the visit schedule of the subject may follow the second branch 186 defined by the mathematical model 110. It is noted that the branching point 182 may not be itself a visit in the visit schedule.

Figure 5:
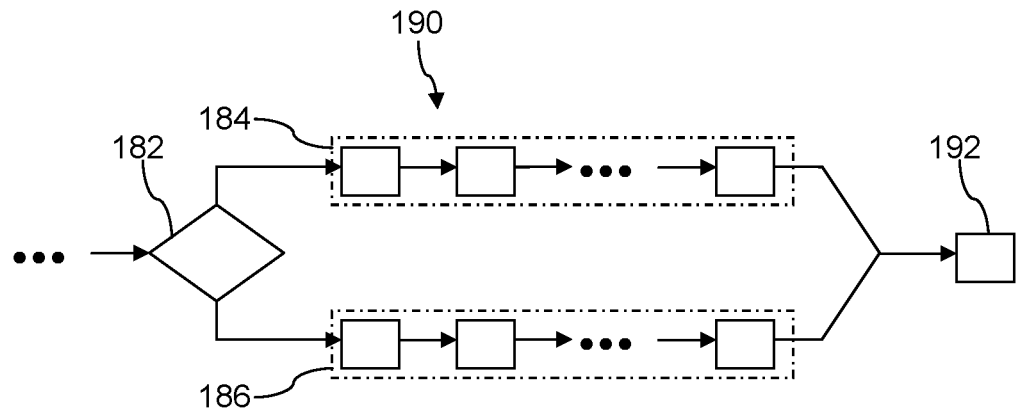
FIG. 5 is an illustration of another branch in a workflow according to an embodiment of the disclosure.
Figure 6:
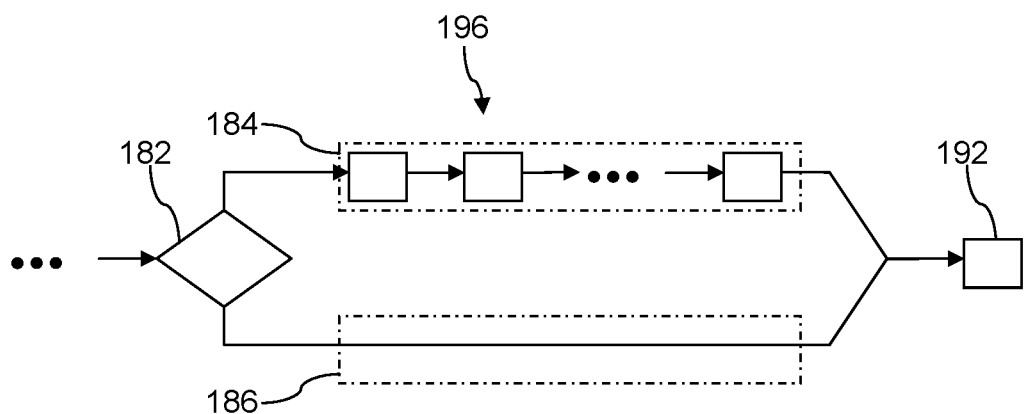
FIG. 6 is an illustration of yet another branch in a workflow according to an embodiment of the disclosure.

Turning now to FIG. 5, a visit schedule 190 that may take one of two different paths at a branching point is described. Basically visit schedule 190 is substantially similar to visit schedule 180, with the exception that both the first branch 184 and the second branch 186 funnel into a same jointure visit 192. The visit schedule may continue with other visits after the jointure visit 192. Turning now to FIG. 6, a visit schedule 196 is described. Basically, visit schedule 196 is substantially similar to visit schedule 190, with the exception that the second branch 186 comprises no visits and the visit schedule 196 proceeds directly to the jointure visit 192. In an embodiment, the jointure visit 192 may be an end-of-trial visit. It is noted that the visit schedule segments and fragments described with reference to FIG. 2, FIG. 3, FIG. 4, FIG. 5, FIG. 6 can be thought of as examples or components of possible visit paths. It is noted that the illustration of visit schedules do not show all dependencies between visits.

Figure 7:
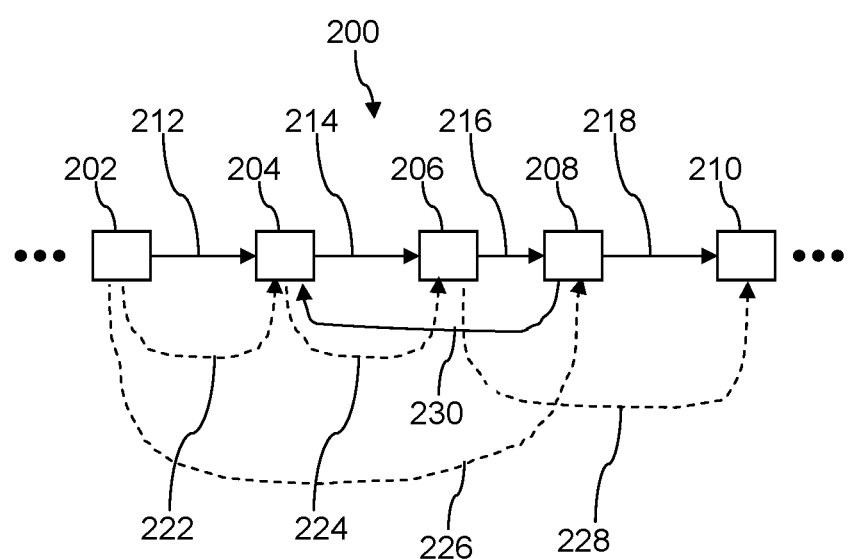
FIG. 7 is an illustration of time-based anchoring and sequence-based anchoring according to an embodiment of the disclosure.

Turning now to FIG. 7, a portion of a visit schedule 200 illustrating dependencies between visits is described. The visit schedule 200 comprises a fifth visit 202, a sixth visit 204, a seventh visit 206, an eighth visit 208, and a ninth visit 210. The sixth visit 204 has a first sequence-based anchor 212 from the fifth visit 202. The seventh visit 206 has a second sequence-based anchor 214 from the sixth visit 204. The eighth visit 208 has a third sequence-based anchor 216 from the seventh visit 206. The ninth visit 210 has a fourth sequence-based anchor 218 from the eighth visit 208. The sixth visit 204 has a first time-based anchor 222 from the fifth visit 202. The seventh visit 206 has a second time-based anchor 224 from the sixth visit 204. The eighth visit 208 has a third time-based anchor 226 from the fifth visit 202. The ninth visit 210 has a fourth time-based anchor 228 from the seventh visit 206. The sixth visit 204 has a fifth time-based anchor 230 from the eighth visit 208. The time-based anchors 222, 224, 226, 228 are forward time-based anchors. The time-based anchor 230 is a reverse time-based anchor.

The sequence-based anchors 212, 214, 216, 218 constrain the visits 202, 204, 206, 208, 210 with reference to their sequence relative to each other. The time-based anchors 222, 224, 226, 228 constrain the visits 202, 204, 206, 208, 210 with reference to the time of occurrence of those visits. The sixth visit 204 is constrained by the first time-based anchor 222 to take place within a first predefined time window after the fifth visit 202 is completed and is constrained by the fifth time-based anchor 230 (a reverse time-based anchor) to take place a second predefined time window before the eighth visit 208. If the calendar date scheduled for the fifth visit 202 changes, the calendar date scheduled for the sixth visit 204 may change too in order to satisfy the constraint defined by the first time-based anchor 222. Additionally, if the calendar date scheduled for the eighth visit 208 changes, the calendar date scheduled for the sixth visit 204 may change too in order to satisfy the constrained defined by the fifth time-based anchor 230. The seventh visit 206 is constrained by the second time-based anchor 224 to take place within a third predefined time window after the sixth visit 204 is completed. If the calendar date scheduled for the sixth visit 204 changes, the calendar data scheduled for the seventh visit 206 may change too in order to satisfy the constraint defined by the second time-based anchor 224. Note that if the calendar date scheduled for the fifth visit 202 changes, the calendar date scheduled for the seventh visit 206 may also change, possibly driven by a change in the calendar date of the sixth visit 204.

The eighth visit 208 is constrained by third time-based anchor 226 to take place within a fourth predefined time window after the fifth visit 202. Note that in the case of the eighth visit 208, if the calendar date scheduled for the sixth visit 204 changes or if the calendar date scheduled for the seventh visit 206 changes, the calendar date of the eighth visit 208 does not necessarily change. The ninth visit 210 is constrained by the fourth time-based anchor 228 to take place within a fifth predefined time window after the seventh visit 206. The workflow management application 104 automatically adjusts and adapts calendar dates for schedules of visits as visits are completed. This provides considerable convenience to research coordinators and assures that protocol defined time-based constraints among visits are not overlooked and broken. Said in other words, while it was easy, when the clinical trials were managed using the spreadsheet with attached sticky notes, to unknowingly blow-past protocol defined visit time windows, the system 100 and the workflow management application 104 of the present disclosure makes it significantly less likely that a research coordinator would not know that a protocol defined time window was at risk. In this way, the workflow management application 104 promotes compliance with clinical trial protocols and contributes to accuracy of performance of clinical trials.

In an embodiment, the workflow management application 104 identifies when a visit of a subject is at risk of going outside the time window and presents a notification on the mobile device 120 of the research coordinator, for example when the research coordinator is scheduling the subject's next visit. The notification of a visit being at risk of going out of window can be related to some other visit than the next visit being scheduled, because of the interactions of constraints (e.g., anchors) associated with other visits. For example, another visit may be constrained to occur after the next visit being scheduled (a sequence anchor) but also constrained to occur no later than a fixed number of days after the baseline visit, and pushing the scheduled date of the next visit out beyond that fixed number of days after the baseline visit means the other visit cannot satisfy both its sequence constraint and its time constraint.

The workflow management application 104 and the workflow management UI 122 help make the research coordinator's life easier and more convenient by allowing him or her to learn at a click of a display screen button what subjects he will see that day and at what time, to learn at a click of a button what activities he needs to perform during that visit with that subject, and to easily indicate he has completed administration of a drug. He can mark activities as completed. He can capture comments and/or values measured during the visit. The workflow management application 104 and workflow management UI 122 also makes the carrying out of clinical trials more consistent and more accurate which can result in more successful and trustworthy clinical trials. Said in another way, the workflow management application 104 and workflow management UI 122 can improve the compliance of clinical trials with the protocol document. For example, because the same mathematical model 110 underlies the functioning of the workflow management application 104 used by a plurality of different research sites, the consistency of processes across the different research sites is promoted. As a side benefit, the process of transcoding the protocol document to the mathematical model 110 involves a rigorous review process that sometimes reveals inconsistencies and errors in the protocol document itself and leads to correcting the protocol document upfront, improving the results of the clinical trial.

Protocol defined events can cause the workflow management application 104 to change the projected visit path of a subject. Example protocol defined events may be death of the subject, a toxic state of the subject (as determined by a diagnostic procedure, a test, or a measurement of vitals), or a stroke experienced by a subject. The occurrence of a protocol defined event may be processed by a branching point such as branching point 182 described above with reference to FIG. 4. The protocol defined event is drawing from the data captured from the patient that is relevant to their response to activities completed during a visit in the clinical trial.

It is understood that the workflow application 104 may implement the workflow management functions described above in a variety of different ways. For example, a subject and the visit schedule associated with the subject and the context information captured from completed visits may be implemented as a linked list, or as a relational database, or in some other data structure. It is understood that the subject visit schedules 112 and the context information objects 114 associated with the same subject may be combined in a single structure rather than in separate structures illustrated in FIG. 1. While the workflow management application 104 is illustrated as a single block in FIG. 1, it is understood that the workflow management application 104 may be implemented as a plurality of separate applications or programs, a library of functions, or in other ways. In an embodiment, the workflow management application 104 may comprise a finance module, a visit schedule management module, and a protocol transcoding application (e.g., a tool that provides computer-assisted transcoding services to a technology worker). The workflow management application 104 may execute in a distributed manner on a plurality of computer systems. While the data store 108 is illustrated as a single entity in FIG. 1, it is understood that the data store 108 may be implemented as multiple separate data stores, multiple virtual storage blocks, multiple logical unit numbers (LUNs), or multiple elastic storage blocks (ESBs). For example, a plurality of modules composing the workflow management application 104 may each have its own separate data store, virtual storage blocks, LUNs, or ESBs.

In addition to functionality that promotes a research coordinator to schedule and perform subject visits, in an embodiment, the workflow management application 104 provides other functionality that promotes higher level management or administration activities across an entire clinical trial or across a plurality of different clinical trials. For example, a research administrator may use the workflow management UI 122 to present a list of all subjects on a second protocol arm of the clinical trial or to present a list of all subjects in a follow-up stage of the clinical trial. For example, a workflow management coordinator may use the workflow management UI 122 to present performance information of the workflow management application 104 across a plurality of different clinical trials supported in a multi-tenancy manner by the workflow management application 104 and the computer system 102.

Figure 8A:
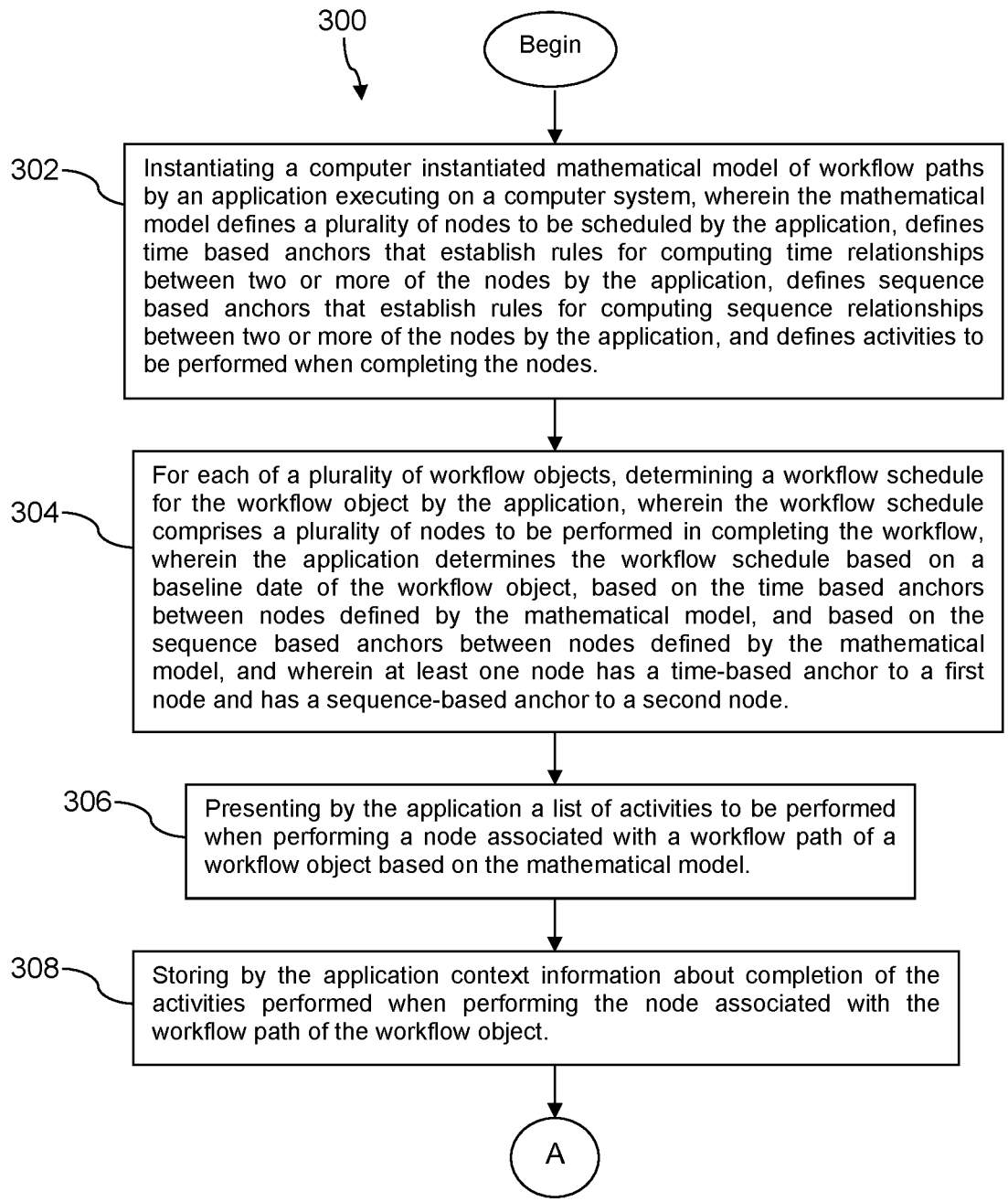
FIG. 8A and FIG. 8B are a flow chart of a method according to an embodiment of the disclosure.
Figure 8B:
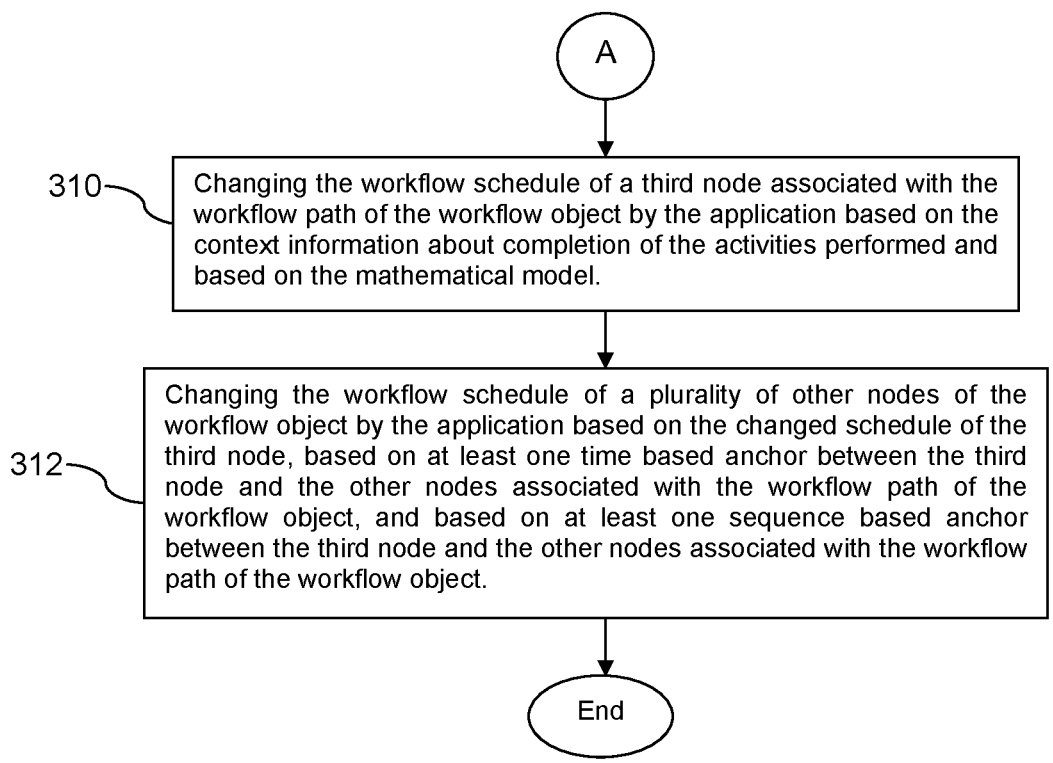

Turning now to FIG. 8A and FIG. 8B, a computer method 300 of managing a workflow of scheduled nodes is described At block 302, the method 300 comprises instantiating a computer instantiated mathematical model ("mathematical model") of workflow paths by an application executing on a computer system, wherein the mathematical model defines a plurality of nodes to be scheduled by the application, defines time-based anchors that establish rules for computing time relationships between two or more of the nodes by the application, defines sequence-based anchors that establish rules for computing sequence relationships between two or more of the nodes by the application, and defines activities to be performed when completing the nodes.

At block 304, the method 300 comprises, for each of a plurality of workflow objects, determining a workflow schedule for the workflow object by the application, wherein the workflow schedule comprises a plurality of nodes to be performed in completing the workflow, wherein the application determines the workflow schedule based on a baseline time of the workflow object, based on the time-based anchors between nodes defined by the mathematical model, and based on the sequence-based anchors between nodes defined by the mathematical model, and wherein at least one node has a time-based anchor to a first node and has a sequence-based anchor to a second node. The baseline time of the workflow object may be the start of the workflow, such as the launch date of a project or the admission of a subject to a clinical trial. The processing of block 304 may determine a partial workflow schedule for the workflow object, for example a workflow schedule comprising two, three, or four of the next nodes to be completed for the workflow object. The workflow object may be a subject of a clinical trial. The workflow object may be a worker who performs a job. The workflow object may be a team of workers collaborating to perform a job. The workflow object may be a subject of a clinical trial. The workflow object may be a worker who performs a job. The workflow object may be a team of workers collaborating to perform a job.

At block 306, the method 300 comprises presenting by the application a list of activities to be performed when performing a node associated with a workflow path of a workflow object based on the mathematical model. At block 308, the method 300 comprises storing by the application context information about completion of the activities performed when performing the node associated with the workflow path of the workflow object.

At block 310, the method 300 comprises changing the workflow schedule of a third node associated with the workflow path of the workflow object by the application based on the context information about completion of the activities performed and based on the mathematical model. For example, the application may process a computational branch and evaluate its associated branching condition defined by the mathematical model based on the context information, and the workflow may branch to a different workflow branch or path defined by the mathematical model that has different nodes associated with it. At block 312, the method 300 comprises changing the workflow schedule of a plurality of other nodes of the workflow object by the application based on the changed schedule of the third node, based on at least one time-based anchor between the third node and the other nodes associated with the workflow path of the workflow object, and based on at least one sequence-based anchor between the third node and the other nodes associated with the workflow path of the workflow object.

Figure 9A:
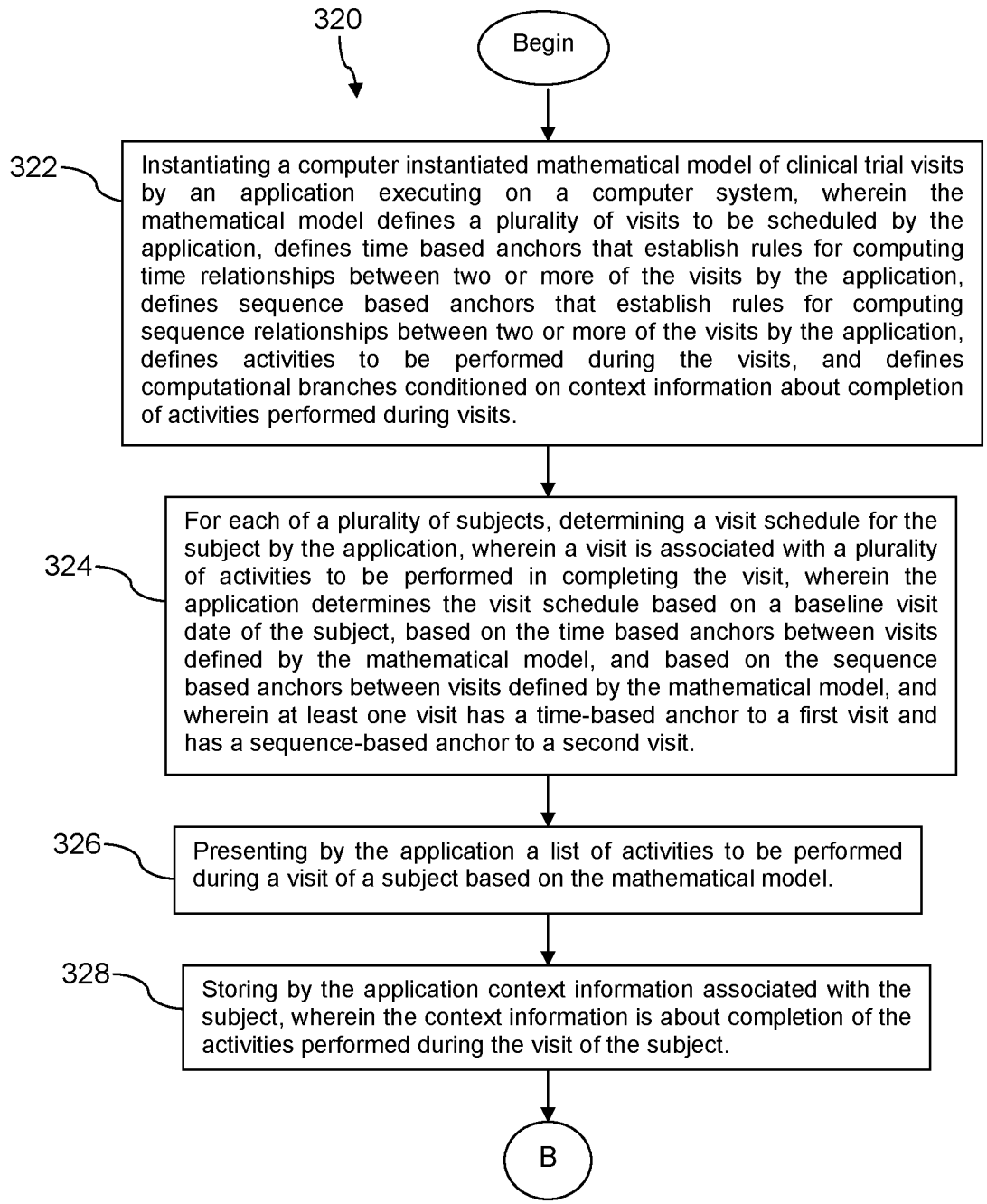
FIG. 9A and FIG. 9B are a flow chart of another method according to an embodiment of the disclosure.
Figure 9B:
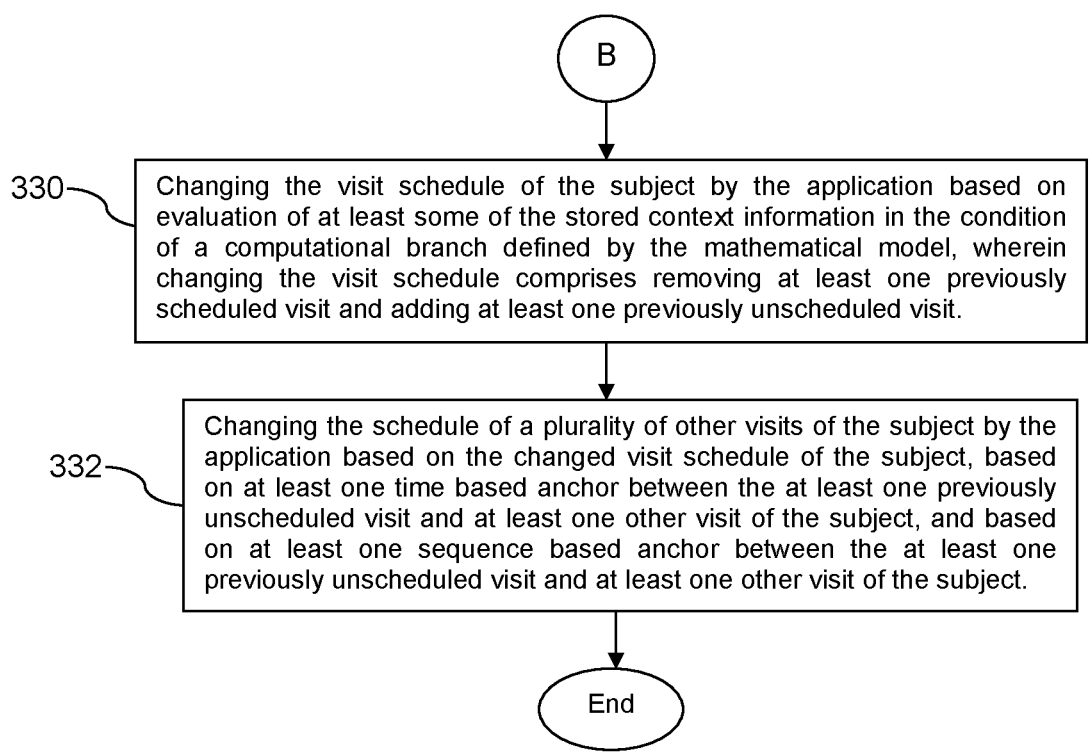

Turning now to FIG. 9A and FIG. 9B, a computer method 320 of managing visits of subjects in a clinical trial is described. At block 322, the method 320 comprises instantiating a computer instantiated mathematical model ("mathematical model") of clinical trial visits by an application executing on a computer system, wherein the mathematical model defines a plurality of visits to be scheduled by the application, defines time-based anchors that establish rules for computing time relationships between two or more of the visits by the application, defines sequence-based anchors that establish rules for computing sequence relationships between two or more of the visits by the application, defines activities to be performed during the visits, and defines computational branches conditioned on context information about completion of activities performed during the visits.

At block 324, the method 300 comprises, for each of a plurality of subjects, determining a visit schedule for the subject by the application, wherein a visit is associated with a plurality of activities to be performed in completing the visit, wherein the application determines the visit schedule based on a baseline visit date of the subject, based on the time-based anchors between visits defined by the mathematical model, and based on the sequence-based anchors between visits defined by the mathematical model, and wherein at least one visit has a time-based anchor to a first visit and has a sequence-based anchor to a second visit. The baseline time may be the date that the subject is evaluated, the date the subject is admitted to the clinical trial, or the date the subject enters the branch of the clinical trial the subject has been randomized to. The visit schedule determined at block 324 may be a partial visit schedule. At block 326, the method 300 comprises presenting by the application a list of activities to be performed during a visit of a subject based on the mathematical model. At block 328, the method 300 comprises storing by the application context information associated with the subject, wherein the context information is about completion of the activities performed during the visit of the subject.

At block 330, the method 320 comprises changing the visit schedule of the subject by the application based on evaluation of at least some of the stored context information in the condition of a computational branch defined by the mathematical model, wherein changing the visit schedule comprises removing at least one previously scheduled visit and adding at least one previously unscheduled visit. At block 332, the method 320 comprises changing the schedule of a plurality of other visits of the subject by the application based on the changed visit schedule of the subject, based on at least one time-based anchor between the at least one previously unscheduled visit and at least one other visit of the subject, and based on at least one sequence-based anchor between the at least one previously unscheduled visit and at least one other visit of the subject.

Figure 10A:
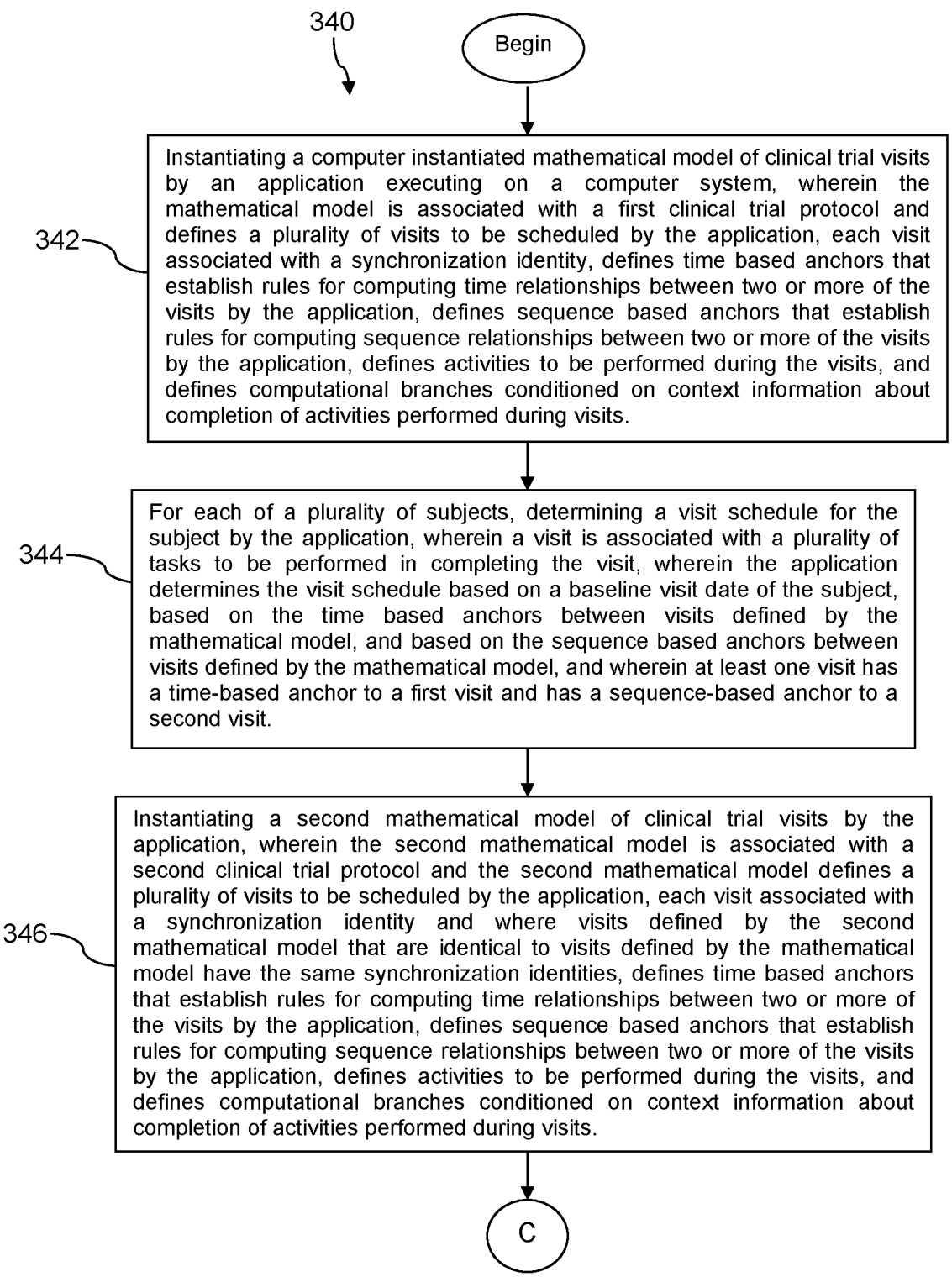
FIG. 10A and FIG. 10B are a flow chart of yet another method according to an embodiment of the disclosure.
Figure 10B:
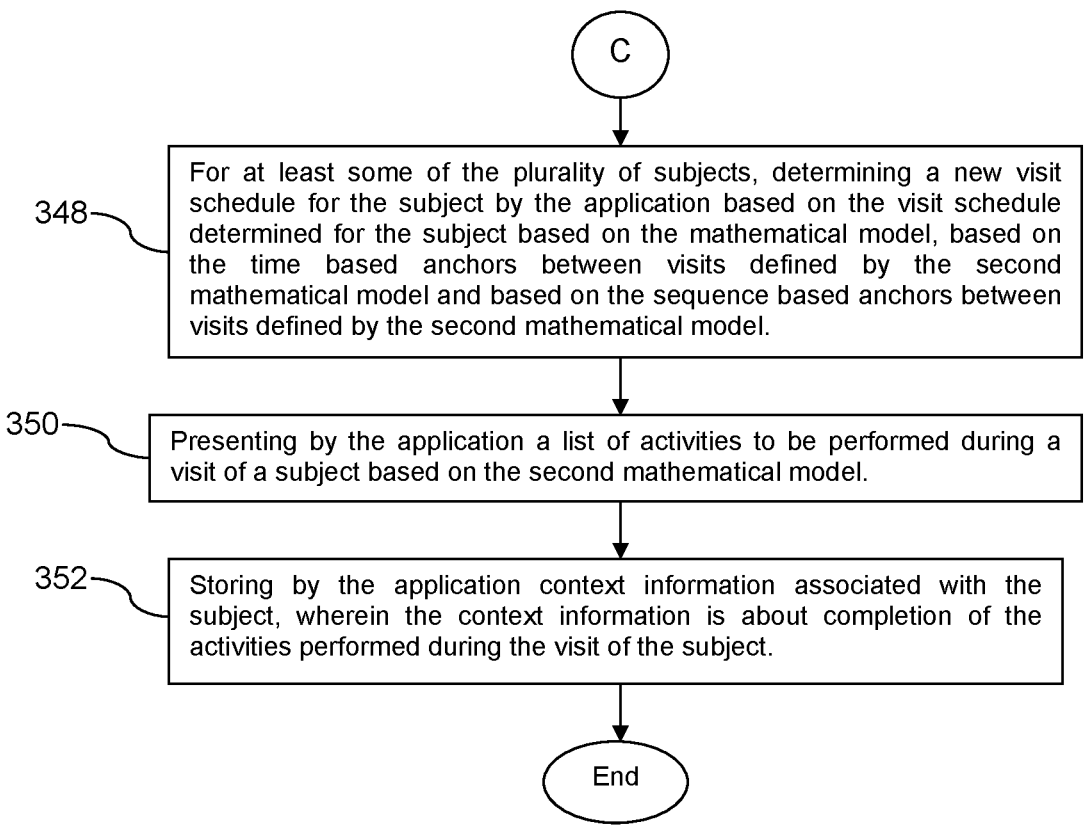

Turning now to FIG. 10A and FIG. 10B, a computer method 340 of managing visits of subjects in a clinical trial is described. At block 342, the method 340 comprises instantiating a computer instantiated mathematical model ("mathematical model") of clinical trial visits by an application executing on a computer system, wherein the mathematical model is associated with a first clinical trial protocol and defines a plurality of visits to be scheduled by the application, each visit associated with a synchronization identity, defines time-based anchors that establish rules for computing time relationships between two or more of the visits by the application, defines sequence-based anchors that establish rules for computing sequence relationships between two or more of the visits by the application, defines activities to be performed during the visits, and defines computational branches conditioned on context information about completion of activities performed during visits. The mathematical model may be built or created based on transcoding a first clinical trial protocol document.

At block 344, the method 340 comprises, for each of a plurality of subjects, determining a visit schedule for the subject by the application, wherein a visit is associated with a plurality of activities to be performed in completing the visit, wherein the application determines the visit schedule based on a baseline visit date of the subject, based on the time-based anchors between visits defined by the mathematical model, and based on the sequence-based anchors between visits defined by the mathematical model, and wherein at least one visit has a time-based anchor to a first visit and has a sequence-based anchor to a second visit. The visit schedule determined at block 344 may be a partial visit schedule.

At block 346, the method 340 comprises instantiating a second mathematical model of clinical trial visits by the application, wherein the second mathematical model is associated with a second clinical trial protocol and the second mathematical model defines a plurality of visits to be scheduled by the application, each visit associated with a synchronization identity and where visits defined by the second mathematical model that are identical to visits defined by the mathematical model have the same synchronization identities, defines time-based anchors that establish rules for computing time relationships between two or more of the visits by the application, defines sequence-based anchors that establish rules for computing sequence relationships between two or more of the visits by the application, defines activities to be performed during the visits, and defines computational branches conditioned on context information about completion of activities performed during visits. The second mathematical model may be built or created based on transcoding a second clinical trial protocol document, for example a revision of the first clinical trial protocol document.

At block 348, the method 340 comprises for at least some of the plurality of subjects, determining a new visit schedule for the subject by the application based on the visit schedule determined for the subject based on the mathematical model, based on the time-based anchors between visits defined by the second mathematical model, and based on the sequence-based anchors between visits defined by the second mathematical model. At block 350, the method 340 comprises presenting by the application a list of activities to be performed during a visit of a subject based on the second mathematical model. At block 352, the method 340 comprises storing by the application context information associated with the subject, wherein the context information is about completion of the activities performed during the visit of the subject.

The method 340 can comprise transferring visits completed before instantiating the second mathematical model to the subjects (e.g., objects maintained by the workflow management application 104 to represent the subjects) who are being transitioned to the second clinical trial protocol. As part of the transferring completed visits, metadata associated with completed visits may be changed to make them conform to the second mathematical model. In some cases changing metadata may result in trivial changes, such as changing names of visits.

Figure 11:
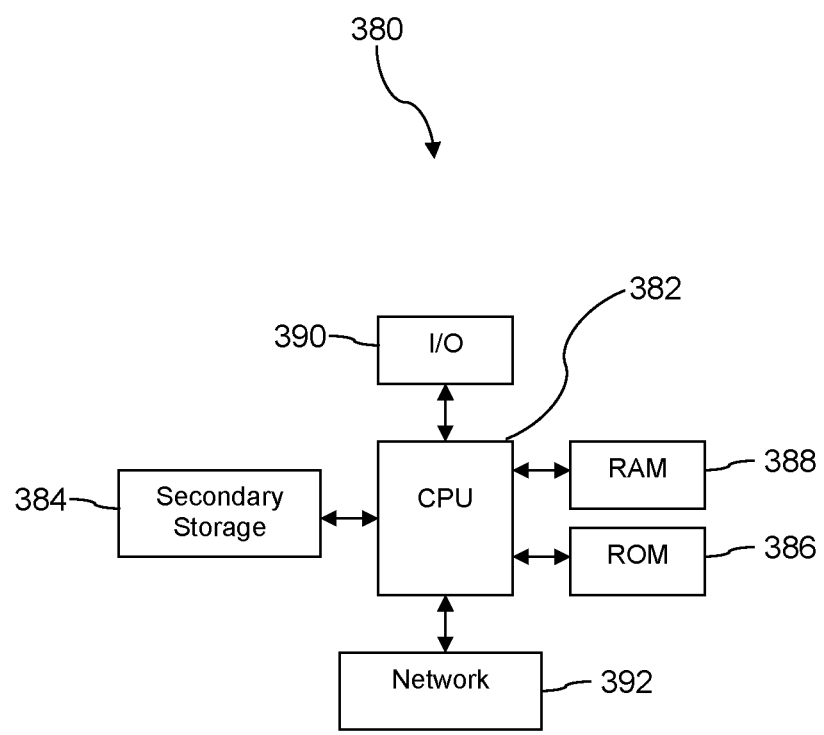
FIG. 11 is a block diagram of a computer system according to an embodiment of the disclosure.

FIG. 11 illustrates a computer system 380 suitable for implementing one or more embodiments disclosed herein. The computer system 380 includes a processor 382 (which may be referred to as a central processor unit or CPU) that is in communication with memory devices including secondary storage 384, read only memory (ROM) 386, random access memory (RAM) 388, input/output (I/O) devices 390, and network connectivity devices 392. The processor 382 may be implemented as one or more CPU chips.

It is understood that by programming and/or loading executable instructions onto the computer system 380, at least one of the CPU 382, the RAM 388, and the ROM 386 are changed, transforming the computer system 380 in part into a particular machine or apparatus having the novel functionality taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

Additionally, after the system 380 is turned on or booted, the CPU 382 may execute a computer program or application. For example, the CPU 382 may execute software or firmware stored in the ROM 386 or stored in the RAM 388. In some cases, on boot and/or when the application is initiated, the CPU 382 may copy the application or portions of the application from the secondary storage 384 to the RAM 388 or to memory space within the CPU 382 itself, and the CPU 382 may then execute instructions that the application is comprised of. In some cases, the CPU 382 may copy the application or portions of the application from memory accessed via the network connectivity devices 392 or via the I/O devices 390 to the RAM 388 or to memory space within the CPU 382, and the CPU 382 may then execute instructions that the application is comprised of. During execution, an application may load instructions into the CPU 382, for example load some of the instructions of the application into a cache of the CPU 382. In some contexts, an application that is executed may be said to configure the CPU 382 to do something, e.g., to configure the CPU 382 to perform the function or functions promoted by the subject application. When the CPU 382 is configured in this way by the application, the CPU 382 becomes a specific purpose computer or a specific purpose machine.

The secondary storage 384 is typically comprised of one or more disk drives or tape drives and is used for non-volatile storage of data and as an over-flow data storage device if RAM 388 is not large enough to hold all working data. Secondary storage 384 may be used to store programs which are loaded into RAM 388 when such programs are selected for execution. The ROM 386 is used to store instructions and perhaps data which are read during program execution. ROM 386 is a non-volatile memory device which typically has a small memory capacity relative to the larger memory capacity of secondary storage 384. The RAM 388 is used to store volatile data and perhaps to store instructions. Access to both ROM 386 and RAM 388 is typically faster than to secondary storage 384. The secondary storage 384, the RAM 388, and/or the ROM 386 may be referred to in some contexts as computer readable storage media and/or non-transitory computer readable media.

I/O devices 390 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 392 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards that promote radio communications using protocols such as code division multiple access (CDMA), global system for mobile communications (GSM), long-term evolution (LTE), worldwide interoperability for microwave access (WiMAX), near field communications (NFC), radio frequency identity (RFID), and/or other air interface protocol radio transceiver cards, and other well-known network devices. These network connectivity devices 392 may enable the processor 382 to communicate with the Internet or one or more intranets. With such a network connection, it is contemplated that the processor 382 might receive information from the network, or might output information to the network in the course of performing the above-described method steps. Such information, which is often represented as a sequence of instructions to be executed using processor 382, may be received from and outputted to the network, for example, in the form of a computer data signal embodied in a carrier wave.

Such information, which may include data or instructions to be executed using processor 382 for example, may be received from and outputted to the network, for example, in the form of a computer data baseband signal or signal embodied in a carrier wave. The baseband signal or signal embodied in the carrier wave, or other types of signals currently used or hereafter developed, may be generated according to several methods well-known to one skilled in the art. The baseband signal and/or signal embedded in the carrier wave may be referred to in some contexts as a transitory signal.

The processor 382 executes instructions, codes, computer programs, scripts which it accesses from hard disk, floppy disk, optical disk (these various disk based systems may all be considered secondary storage 384), flash drive, ROM 386, RAM 388, or the network connectivity devices 392. While only one processor 382 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 384, for example, hard drives, floppy disks, optical disks, and/or other device, the ROM 386, and/or the RAM 388 may be referred to in some contexts as non-transitory instructions and/or non-transitory information.

In an embodiment, the computer system 380 may comprise two or more computers in communication with each other that collaborate to perform a processing job. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computer system 380 to provide the functionality of a number of servers that is not directly bound to the number of computers in the computer system 380. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an embodiment, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 380, at least portions of the contents of the computer program product to the secondary storage 384, to the ROM 386, to the RAM 388, and/or to other non-volatile memory and volatile memory of the computer system 380. The processor 382 may process the executable instructions and/or data structures in part by directly accessing the computer program product, for example by reading from a CD-ROM disk inserted into a disk drive peripheral of the computer system 380. Alternatively, the processor 382 may process the executable instructions and/or data structures by remotely accessing the computer program product, for example by downloading the executable instructions and/or data structures from a remote server through the network connectivity devices 392. The computer program product may comprise instructions that promote the loading and/or copying of data, data structures, files, and/or executable instructions to the secondary storage 384, to the ROM 386, to the RAM 388, and/or to other non-volatile memory and volatile memory of the computer system 380.

In some contexts, the secondary storage 384, the ROM 386, and the RAM 388 may be referred to as a non-transitory computer readable medium or a computer readable storage media. A dynamic RAM embodiment of the RAM 388, likewise, may be referred to as a non-transitory computer readable medium in that while the dynamic RAM receives electrical power and is operated in accordance with its design, for example during a period of time during which the computer system 380 is turned on and operational, the dynamic RAM stores information that is written to it. Similarly, the processor 382 may comprise an internal RAM, an internal ROM, a cache memory, and/or other internal non-transitory storage blocks, sections, or components that may be referred to in some contexts as non-transitory computer readable media or computer readable storage media.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A computer method of managing a workflow of scheduled nodes, comprising:

instantiating a computer instantiated mathematical model of workflow paths by an application executing on a computer system, wherein the computer instantiated mathematical model manages a subject in a clinical trial on a projected visit path, defines a plurality of nodes to be scheduled by the application, defines time-based anchors that establish rules for computing time relationships between two or more of the plurality of nodes by the application, defines sequence-based anchors that establish rules for computing sequence relationships between two or more of the plurality of nodes by the application, defines activities to be performed when completing the plurality of nodes, and defines a plurality of computational branches and a plurality of associated branching conditions, wherein the time-based anchors comprise forward time-based anchors, and wherein each of the forward time-based anchors is defined in the computer instantiated mathematical model to extend from an earlier node to a later node and constrain the later node to be completed within a designated time span after the earlier node by being built into a computer instantiated structure representing the earlier node that identifies the later node to which the computer instantiated structure representing the earlier node logically attaches and the designated time span within which the later node is constrained to occur after the earlier node;

for each of a plurality of workflow objects, determining a workflow schedule for the workflow object by the application, wherein the workflow schedule comprises at least a subset of the plurality of nodes to be performed in completing the workflow, wherein the application determines the workflow schedule based on a baseline time of the workflow object, based on the time-based anchors between nodes in the subset defined by the computer instantiated mathematical model, and based on the sequence-based anchors between nodes in the subset defined by the computer instantiated mathematical model, and wherein at least one node in the subset has a forward time-based anchor to a first node in the subset and has a sequence-based anchor to a second node in the subset;

presenting by the application a list of activities to be performed when performing a node in the subset associated with a workflow path of a workflow object based on the computer instantiated mathematical model;

storing, by the application, context information about completion of the activities performed when performing the node in the subset associated with the workflow path of the workflow object;

changing a workflow schedule of a third node in the subset associated with the workflow path of the workflow object by the application based on the context information about completion of the activities performed and based on the computer instantiated mathematical model;

changing a workflow schedule of a plurality of other nodes in the subset associated with the workflow path of the workflow object by the application based on the changed workflow schedule of the third node, based on at least one time-based anchor between the third node and the plurality of other nodes associated with the workflow path of the workflow object, and based on at least one sequence-based anchor between the third node and the plurality of other nodes associated with the workflow path of the workflow object;

determining, by the application, that a branching condition has occurred based on context information about completion of activities performed during visits on the projected visit path;

in response to the determination that the branching condition has occurred, placing, by the application, the subject on a new visit path for the clinical trial different from the projected visit path, wherein the new visit path removes at least one previously scheduled visit that had been defined by the projected visit path and adds at least one previously unscheduled visit that was not defined for the projected visit path; and in response to placing the subject on the new visit path and based on parsing the computer instantiated mathematical model, determining, by the application, an updated projected visit path for the subject using the time-based anchors and the sequence-based anchors of the nodes that are defined for the new visit path.

2. The computer method of claim 1, wherein the workflow schedule is a partial workflow schedule.

3. The computer method of claim 1, wherein the computer instantiated mathematical model further defines at least one repetitive node cycle, where the at least one repetitive node cycle comprises at least two nodes that repeat in the workflow schedule.

4. The computer method of claim 3, where the at least one repetitive node cycle repeats until a cycle exit condition defined by the computer instantiated mathematical model is satisfied.

5. The computer method of claim 3, where the at least one repetitive node cycle repeats until the workflow object is one of destroyed or discarded.

6. The computer method of claim 1, further comprising transitioning the subject from a first protocol of the clinical trial to a second protocol of the clinical trial by instantiating a second computer instantiated mathematical model corresponding to the second protocol of the clinical trial, wherein the second computer instantiated mathematical model is created by copying the computer instantiated mathematical model corresponding to the first protocol of the clinical trial including the time-based anchors and the sequence-based anchors defined by the computer instantiated mathematical model, modifying one or more visits copied from the computer instantiated mathematical model by modifying at least one of the time-based anchors or the sequence-based anchors copied from the computer instantiated mathematical model, and adding one or more visits to the second computer instantiated mathematical model not present in the first computer instantiated mathematical model.

7. A computer method of managing visits of subjects in a clinical trial, comprising:

instantiating a computer instantiated mathematical model ("mathematical model") of clinical trial visits by an application executing on a computer system, wherein the computer instantiated mathematical model is associated with a first clinical trial protocol, defines a plurality of visits to be scheduled by the application, defines time-based anchors that establish rules for computing time relationships between two or more of the plurality of visits by the application, defines sequence-based anchors that establish rules for computing sequence relationships between two or more of the plurality of visits by the application, defines activities to be performed during the plurality of visits, and defines computational branches conditioned on context information about completion of activities performed during the plurality of visits, wherein the time-based anchors comprise forward time-based anchors, and wherein each of the forward time-based anchors is defined in the computer instantiated mathematical model to extend from an earlier visit to a later visit and constrain the later visit to be completed within a designated time span after the earlier visit by being built into a computer instantiated structure representing the earlier visit that identifies the later visit to which the computer instantiated structure representing the earlier visit logically attaches and the designated time span within which the later visit is constrained to occur after the earlier visit;

for each of a plurality of subjects, determining a visit schedule for the subject by the application, wherein a visit is associated with a plurality of activities to be performed in completing the visit, wherein the application determines the visit schedule based on a baseline visit date of the subject, based on the time-based anchors between at least a subset of the plurality of visits defined by the computer instantiated mathematical model, and based on the sequence-based anchors between visits of the subset defined by the computer instantiated mathematical model, and wherein at least one visit of the subset has a forward time-based anchor to a first visit of the subset and has a sequence-based anchor to a second visit of the subset;

presenting by the application a list of activities to be performed during a visit of the subset with a subject based on the computer instantiated mathematical model;

storing, by the application, context information associated with the subject, wherein the context information is about completion of the activities performed during the visit of the subject;

changing the visit schedule of the subject by the application based on evaluation of at least some of the stored context information matching a condition of a computational branch defined by the computer instantiated mathematical model, wherein changing the visit schedule comprises removing at least one previously scheduled visit and adding at least one previously unscheduled visit;

changing a schedule of a plurality of other visits of the subject by the application based on the changed visit schedule of the subject, based on at least one time-based anchor between the at least one previously unscheduled visit and at least one other visit of the subject, and based on at least one sequence-based anchor between the at least one previously unscheduled visit and at least one other visit of the subject;

instantiating a second computer instantiated mathematical model of clinical trial visits by the application, wherein the second computer instantiated mathematical model is associated with a second clinical trial protocol and the second computer instantiated mathematical model defines a plurality of visits to be scheduled by the application, each visit defined by the second computer instantiated mathematical model associated with a synchronization identity and where visits defined by the second computer instantiated mathematical model that are identical to visits defined by the computer instantiated mathematical model have the same synchronization identities, defines time-based anchors that establish rules for computing time relationships between two or more of the plurality of visits defined by the second computer instantiated mathematical model by the application, defines sequence-based anchors that establish rules for computing sequence relationships between two or more of the plurality of visits defined by the second computer instantiated mathematical model by the application, defines activities to be performed during the plurality of visits defined by the second computer instantiated mathematical model, and defines computational branches conditioned on context information about completion of activities performed during the plurality of visits defined by the second computer instantiated mathematical model;

for at least some of the plurality of subjects, determining a new visit schedule for the subject by the application based on the visit schedule determined for the subject based on the computer instantiated mathematical model, based on the time-based anchors between at least some of the plurality of visits defined by the second computer instantiated mathematical model and based on the sequence-based anchors between at least some of the plurality of visits defined by the second computer instantiated mathematical model;

presenting by the application a list of activities to be performed during another visit of the subject based on the second computer instantiated mathematical model; and storing by the application context information associated with the subject, wherein the context information is about completion of the activities performed during the another visit of the subject.

8. The computer method of claim 7, wherein the clinical trial is associated with testing a medication or testing a medical treatment process.

9. The computer method of claim 7, wherein the computer instantiated mathematical model defines a washout state of subjects, further comprising:
evaluating the context information by the application based on a washout definition; and
when presenting a visit activity list on a display, presenting a notification that the subject is in a washout state by the application.

10. The computer method of claim 9, wherein the computer instantiated mathematical model defines a washout state time duration.

11. The computer method of claim 9, wherein the computer instantiated mathematical model identifies instructions for actions for a subject to perform while in a washout state.

12. The computer method of claim 7, wherein the baseline visit date is a date the subject is evaluated for admission to the clinical trial, a date the subject is admitted to the clinical trial, or a date the subject completes an initial visit after being assigned to a protocol arm of the clinical trial.

13. The computer method of claim 7, wherein at least some of the time-based anchors identify a time relationship as a minimum time value and a maximum time value.

14. The computer method of claim 7, wherein the time-based anchors further comprise reverse time-based anchors, wherein each of the reverse time-based anchors is defined in the computer instantiated mathematical model to extend from a second earlier visit to a second later visit and constrain the second earlier visit to be completed within a designated time span before the second later visit, and wherein at least one visit of the subset has a reverse time-based anchor to one visit of the subset and has a sequence-based anchor to another visit of the subset.

15. The computer method of claim 7, further comprising:
parsing a clinical trial protocol document by a protocol transcoding application that executes on the computer system;
analyzing the clinical trial protocol document by the protocol transcoding application based on the parsing; and
automatically generating the computer instantiated mathematical model by the protocol transcoding application based on analyzing the clinical trial protocol document, whereby the protocol transcoding application automatically transcodes the clinical trial protocol document into the computer instantiated mathematical model.

16. The computer method of claim 7, further comprising transferring visits completed before instantiating the second computer instantiated mathematical model to a plurality of subjects who are moved to the second clinical trial protocol by the application.

17. The computer method of claim 16, further comprising changing metadata associated with some of the transferred visits by the application to make them conform to the second computer instantiated mathematical model.

18. The computer method of claim 7, further comprising presenting by the application descriptions of procedures for performing the activities in the presented activities list.

* * * * *